United States Patent [19]

Cahen et al.

[11] Patent Number: 4,533,252

[45] Date of Patent: Aug. 6, 1985

[54] DEVICE AND METHOD AND MEASUREMENT OF PHOTOSYNTHETIC ACTIVITY BY PHOTOACOUSTIC SPECTROSCOPY

[75] Inventors: David Cahen; Shmuel Malkin; Benjamin Horwitz, all of Rehovot, Israel; Gerard Bults, Wageningen, Netherlands

[73] Assignee: Yeda Research and Development Company Ltd., Rehovot, Israel

[21] Appl. No.: 381,767

[22] Filed: May 25, 1982

[30] Foreign Application Priority Data

Jun. 5, 1981 [IL] Israel .................................. 63053

[51] Int. Cl.³ .......................................... G01N 21/24
[52] U.S. Cl. .................................... 356/432; 356/440
[58] Field of Search ........................ 356/432, 440; 250/461.1

[56] References Cited

U.S. PATENT DOCUMENTS

| 4,028,932 | 6/1977 | Rosencwaig | 73/571 |
| 4,129,385 | 12/1978 | Rosencwaig et al. | 356/432 |
| 4,376,890 | 3/1983 | Engstrom et al. | 250/461.1 |

Primary Examiner—R. A. Rosenberger
Attorney, Agent, or Firm—Browdy and Neimark

[57] ABSTRACT

A portable device for photoacoustic spectroscopy of plants and other photosynthetic tissues, cells and organelles is provided. There is further provided a method of measuring photosynthesis of such tissues, cells and organelles.

10 Claims, 11 Drawing Figures

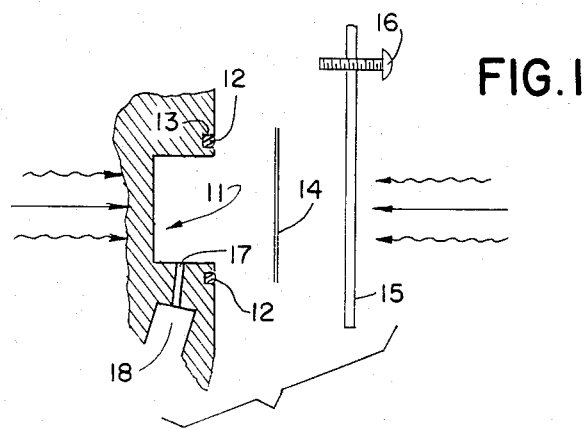
FIG. 1
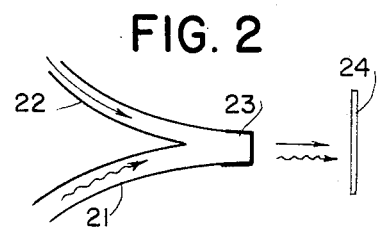
FIG. 2
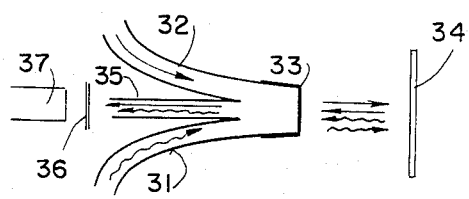
FIG. 3
FIG. 4
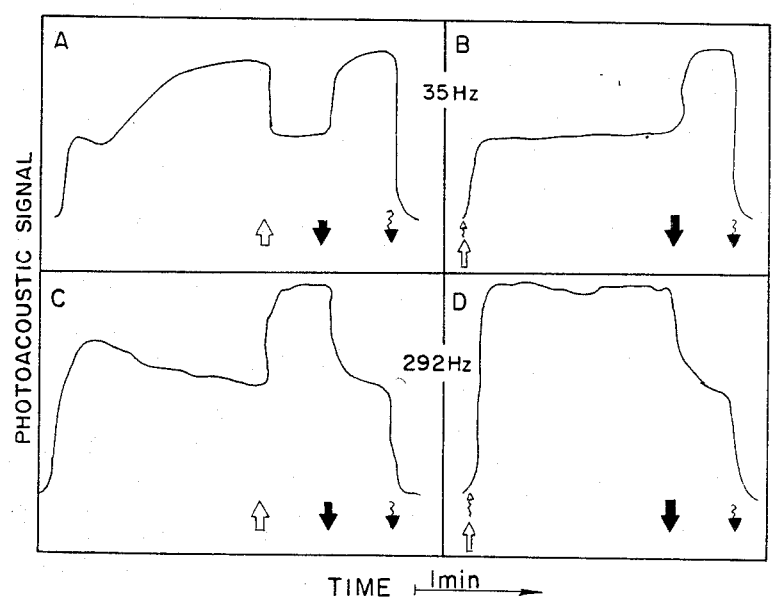

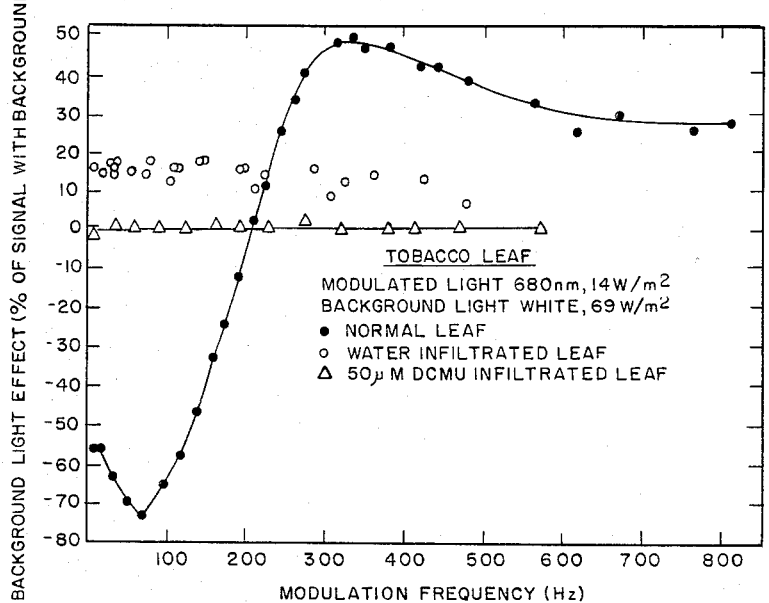
FIG. 7
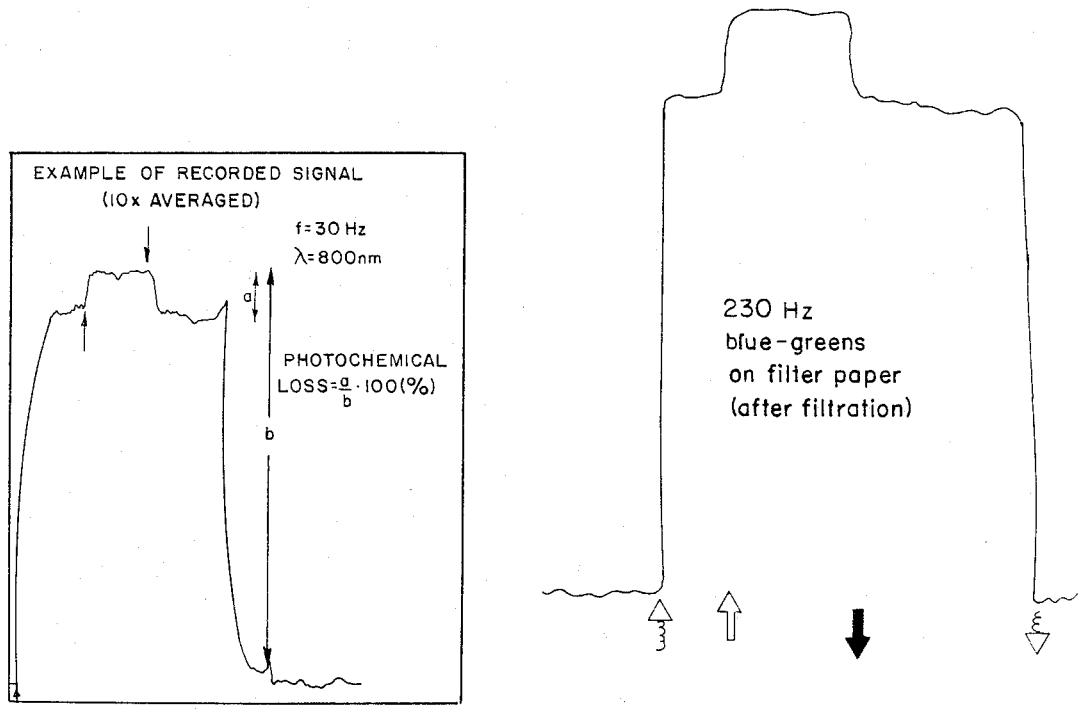
FIG. 8
FIG. 9

DEVICE AND METHOD AND MEASUREMENT OF PHOTOSYNTHETIC ACTIVITY BY PHOTOACOUSTIC SPECTROSCOPY

FIELD OF THE INVENTION

The present invention relates to a novel device for carrying out photoacoustic measurements, especially in the field and on living plants. The novel device is a portable one and can be easily moved from place to place and actuated at short notice.

The invention further relates to a method of measurement of the photosynthetic activity of various kinds of photosynthetic tissues, such as leaves, protoplasts, algae and bacterial cells by means of such novel device.

BACKGROUND OF THE INVENTION

A photoacoustic (PA) signal can be obtained when a sample, situated in a gas-filled closed chamber, is illuminated by a beam of light (or other radiation), the intensity of which varies at an acoustic frequency. If the sample absorbs the light, its periodic excitation leads to periodic heating (thermal wave). This wave, when transferred to a thin boundary layer of gas, generates a pressure wave at an acoustic frequency, which is detected by a microphone in the sample chamber. The microphone signal is a measure of that part of the absorbed light that is converted into heat, and, if all the absorbed energy becomes heat (i.e. only thermal decay of the excited states occurs) the PA signal can correspond to the optical absorption by the sample. However, if some of the absorbed light is re-emitted (luminescence) or converted into (electro) chemical or electrical energy, the PA signal can differ significantly from the optical absorption signal, by an amount called "photochemical-loss" (PL) (S. Malkin and D. Cahen, Photochem. Photobiol. 29, 803 (1979)).

Gray et al., Anal. Chem. 50 1262 (1978), have described photoacoustic spectroscopy applied to systems involving photoinduced gas evolution or consumption. Their investigation relates to non-biological samples and their measurements were carried out with a conventional photoacoustic cell. Fishman et al., Anal. Chem. 53, 102 (1981), deal with open-ended photoacoustic spectroscopy cells for thin layer chromatography and other applications. The cell used is one where the sample forms one wall of said cell, and the closure is due to the sheer weight of the cell. The signal to noise ratio is low and such cell is comparatively massive and can only be used with smooth surfaces. The measurements were effected on precoated hard-layer TLC plates.

None of the hitherto known devices was applied to the measurement of photosynthesis of intact photosynthetic tissues in vivo, such as leaves of living plants, algae and bacteria, and hitherto no mobile instrument for this purpose is known.

The only methods tried until now in this respect are thermal radiometry (measurement of the leaf skin temperature by IR detectors), preferably in two dimensions to get a temperature profile of the leaf or plant. A method used nowadays in the laboratory measures the carbon dioxide uptake of plants. It is rather cumbersome and time consuming and not field-adaptable.

SUMMARY OF THE INVENTION

The invention relates to a novel mobile photoacoustic cell (PAC), which is portable and which can be used for photosynthetic measurements of photosynthetic tissues (leaves, etc.).

The invention furthermore relates to a method of photoacoustic measurements of photosynthetic tissues (leaves, etc.).

The novel photoacoustic cell comprises a housing, open at one end, which end is closed in use by the sample, such as a leaf to be measured, which is tightly clamped in place by suitable clamping means. There is provided a source of continuous light, a source of modulated light and a suitable transducer, such as a sensitive microphone, located in said housing. According to a preferred embodiment there is used a bifurcated (double, i.e. two branches) light-guide for both non-modulated continuous (background) and for modulated lights; according to another embodiment there is used a triple light guide (three branches), having a common end adapted to be positioned close to the sample which is being examined, said triple light guide serving for conducting continuous and modulated light towards the sample, and luminescence from the sample via a filter to a photo-detector.

The wavelength used for the illumination is preferably in the range of 400–750 nm and the wavelength of fluorescence detection is in the range of 670–800 nm. For bacterial cultures the above wavelength range extends to the near IR (illumination: 400–900 nm; fluorescence: 850–1000 nm).

There were carried out measurements on leaves, algae and bacterial cells, in combination with the technique of background light referencing.

The housing can be transparent and the light is introduced either through said housing via a light-guide or via the sample, or both.

The invention is illustrated in greater detail in the following. It is stressed that the description is by way of illustration only and that various modifications and changes both in the construction of the device as well as in the method of measurement can be resorted to without departing from the scope and spirit of the invention.

BRIEF DESCRIPTION OF THE DRAWINGS

The novel photoacoustic cell (PAC) is illustrated with reference to the enclosed schematical drawing, now according to scale, wherein FIG. 1 is an exploded schematic sectional side view of the device;

FIG. 2 is a schematic sectional side view of a bifurcated light guide;

FIG. 3 is a sectional side view of a triple light guide;

FIG. 4 illustrates photoacoustic signals obtained during measurements according to the present invention;

FIG. 7 illustrates also the effect of water and DCMU infiltration into a leaf;

FIG. 8 illustrates the effect of background light for bacterial cells;

FIG. 9 illustrates the effect of background light for algal cultures;

DESCRIPTION OF THE PREFERRED EMBODIMENT

Figure 5:
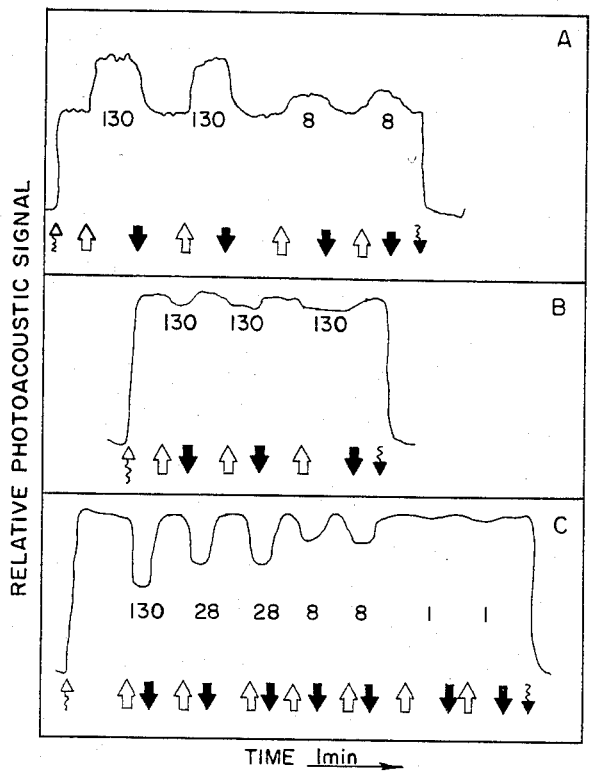
FIG. 5 illustrates the effect of background light application in the steady state at various frequencies and various background light intensities.

As shown in FIG. 1 the photoacoustic cell according to the invention comprises in combination a housing 11 provided with a groove 12 adapted to fit O-ring 13, said cell being open at one end, said end being adapted to be closed by means of, or enclose the sample 14 to be measured and by means of a glass plate 15 which is attached under pressure to the cell-housing 11 by suitable means such as a clamp and screws 16. A channel 17 is provided in one of the side-walls of the housing 11 and a transducer 18 is located at the end of said channel.

A representative internal volume of such cell is of the order of 0.05–2 cm$^3$. There may be used a bifurcated light guide as illustrated in FIG. 2, comprising a light guide 21 for modulated light and a light guide 22 for continuous light, said light guides terminating in the common end 23, said common end being located during the measurement adjacent to the sample 24.

According to a preferred embodiment there is used a triple light guide as illustrated in FIG. 3, which comprises a light guide 31 for modulated light, a light guide 32 for continuous light and a light guide 35 for the luminescent radiation from the sample 34 which is led via said light guide 35 and via optical filter 36 to the photodetector 37, said light guides terminating at the common end 33 adjacent to the sample 34.

The housing can be transparent. It can also be provided with an opening through which a light guide is inserted.

Leaf strips of ca. 2×3 cm were cut from mature tobacco plants (*Nicotiana tabacum* var. Xanthi) or whole leaves from *Caragana Arborescens Lam.* (Siberian pea) were used and placed in a photoacoustic cell as described above. When desired, leaf strips were vacuum infiltrated with water or inhibitor solutions.

Mechanically chopped light from a standard projector or a 450 W Xe-lamp was passed through water and interference filters (Schott). A bifurcated randomized light guide according to FIG. 2 was used to direct both modulated (680 nm, 14 W/m$^2$; intensities as low as 1 W/m$^2$ and over 40 W/m$^2$ can be effectively used) and saturating DC background light (400–720 nm, 340 W/m$^2$) onto the sample. The microphone signal was fed into a lock-in amplifier (Ortholoc 9502, Brookdeal) and recorded.

FIG. 4A shows the photoacoustic signal measured at 35 Hz for a dark-adapted leaf. During an induction period of about 2 minutes there is an increase in signal with biphasic kinetics, tending to a steady state level. Background light application lowers the signal to its initial level. The photoacoustic signal measured at 292 Hz (FIG. 4C) shows, on the other hand, a transient *decrease* during the same period. This behavior during the induction period is the reverse of that observed at the lower frequency. Application of strong background light which saturates photosynthetic activity results in a 50% increase in signal, appreciably higher than in isolated broken chloroplasts.

Transients are not observed if saturating background light is applied from the start of illumination of dark-adapted leaves (FIGS. 4B and 4D). This shows that both the low and high frequency transients are associated with photochemistry and that they do not involve changes in the thermal parameters. Such changes should persist also in the presence of background light, which obviously is not the case. Moreover, one would expect the changes at low and high modulation frequencies to be in the same direction, again in contrast with the experimental results (FIGS. 4A and 4C).

The low frequency signal is composed of two mechanistically independent contributions: one is due to the usual conversion of modulated heat to modulated pressure, the second is due to oxygen evolution, which is partly modulated (photobaric effect), and hence results directly in pressure modulation. (Indeed, if, re-emitted IR radiation is monitored (cf. Physica Scripta 20, 659 [1979]; App.Phys.Lett. 38, 486 [1981]), only the signal due to modulated heat is sensed and the resulting signal, at low frequencies, closely resembles that observed acoustically at high frequencies.) Using a fast-responding oxygen electrode, P. Joliot et al. (J.Chim.Phys., 63, 1423 (1966)), were able to detect modulated oxygen evolution from chloroplasts and algae at frequencies as high as 200 Hz, the signal being strongly damped as the frequency increased. Oxygen uptake by the photooxidation of rubrene or photocatalytic decomposition of acetic acid have been followed before by photoacoustic spectroscopy. Calculations were made of the possible contribution of modulated oxygen evolution to the signal, using independently determined values for the sensitivity of the microphone/cell combination. They are in agreement with the observed decrease in the low frequency photoacoustic signal upon saturation with background light (FIG. 4A). Furthermore, according to these calculations, the oxygen evolution component becomes too small to be detected above 200 Hz. This component is progressively damped with increasing frequency because of the time required for oxygen diffusion from the chloroplasts to the gas phase. Thus at high frequency only the photochemical loss persists, and the transient decrease in this case (FIG. 4C) reflects the gradual onset of photochemistry, lowering the measured heat release upon light absorption during photosynthetic induction. Modulated $CO_2$ uptake does not contribute significantly to the signal, being strongly damped due to successive intermediary reactions, involving relatively slow rate constants and large pool sizes, which separate between the photoact and $CO_2$ uptake.

FIG. 5 shows steady-state measurements, the interpretation of which is again that at low frequencies (FIG. 5C; 15 Hz) the change introduced by background light is due to oxygen evolution and that at high frequencies (FIG. 5A; 425 Hz), it is due to photochemical energy storage, both effects measuring photosynthetic activities. An intermediate effect is obtained at intermediate frequencies (FIG. 5B; 150 Hz). The numbers in the Figure give the background light intensity (in W/m$^2$ used).

Figure 6:
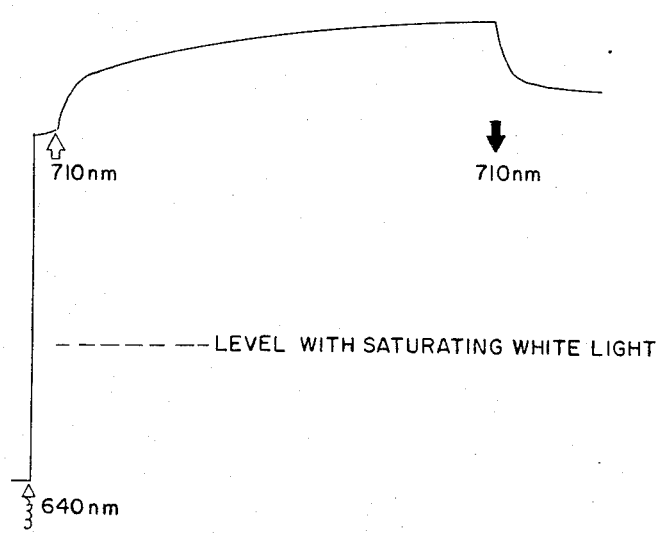
FIG. 6 illustrates the effect of background light to investigate the relative importance of the two photosystems ("enhancement")

FIG. 6 shows the use of measurements, such as those shown in FIG. 4 to follow the distribution of incident illumination between the two photosystems in green plant leaves. If modulated light is used that is effective mainly in exciting photosystem I (II), an enhancement of photochemical activity (i.e. oxygen evolution) is seen when continuous background light is used that is effective mainly in exciting photosystem II (I), while no such effect is seen when "white" continuous background light is used. Such measurements are useful, for example, for studying the effects of environmental conditions on the photosystems separately, or for following the effects of genetic manipulations on these (e.g. in plant breeding). While the effects are illustrated here for leaves of tobacco plants, they are found for leaves of all species investigated to date, including varieties of wheat, barley, cabbage, bean, pea, mint, spinach, etc.).

Leaves, vacuum infiltrated with DCMU (3-(3,4-dichlorophenyl)-1,1-dimethyl urea) solutions (50 $\mu M$) do not show any transients or effect of background light at any frequency (FIG. 7). Water-infiltrated leaves, however, show a ca. 15% photochemical loss from 10 to 300 Hz. The oxygen evolution component in the photoacoustic signal was lost (damped) in this case, as the diffusion path of oxygen increased (from ca. 1 $\mu$m—the average chloroplast to cell wall distance—to an average of ca. 30 $\mu$m—the distance to the leaf surface in the case where water fills the intercellular spaces). The thermal component was also damped but not as much. A further indication that the low frequency transient (FIG. 4) reflects photosynthetic oxygen evolution is its similarity to the reported induction pattern of oxygen evolution in leaves, (see D. A. Walker New Phytology 72, 209 (1973)).

FIG. 8 shows the basic effect (FIG. 5A) for bacterial cells of *Rhodospirillum rubrum*. Here near IR radiation is used as modulated light. The calculation of the PL is illustrated, as well. Here bacteriochlorophyll is the main absorbing pigment. As photosynthetic bacteria do not evolve oxygen, only effects of signal increase, upon application of background light, are observed.

FIG. 9 shows the basic effect (FIG. 5A) for algal cultures of *Nostoc muscorum* (strain 7119) at high frequencies. Here a volume (~10 ml) of algal culture solution was filtered and the photoacoustic cell was attached to the filter paper on which the algae were deposited.

Figure 10:
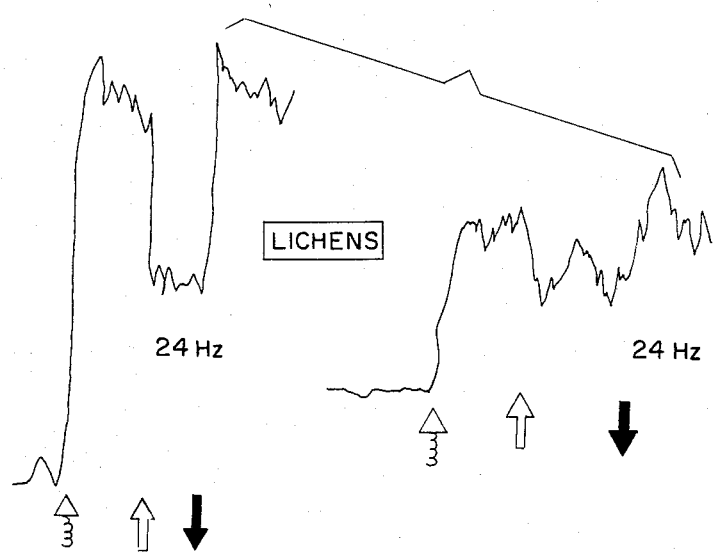
FIG. 10 illustrates the effect of background light for some types of lichens.

FIG. 10 illustrates how the effect can be used to evaluate the state of lichens. The signals obtained from active species are compared to those of less active ones. Samples of lichens were placed on glass slides for this kind of investigation.

Figure 11:
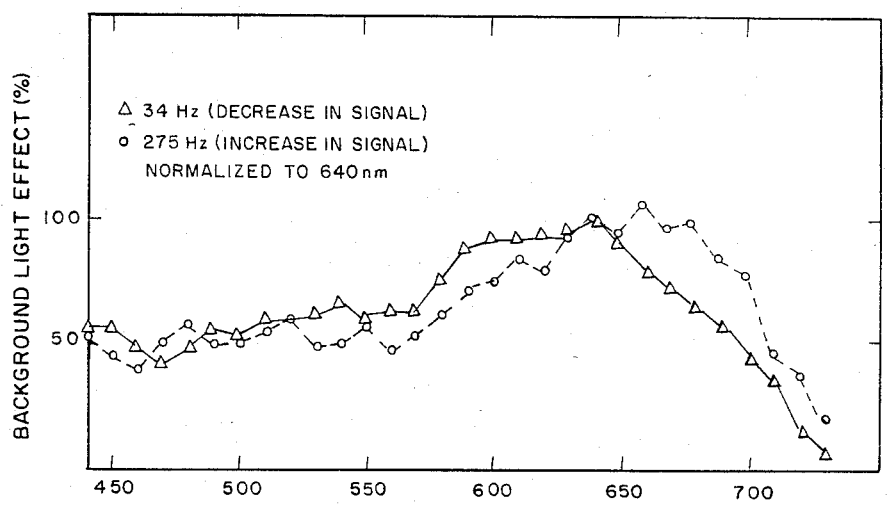
FIG. 11 illustrates the wavelength dependence (quantum yield spectra, of photosynthetic/photoacoustic measurements as done in FIG. 5).

FIG. 11 demonstrates how the above results, scanned over the wavelength of the modulated light are applied to obtain the relative activity at various parts of the spectrum. The extent of the background light effect is proportional to the quantum yield. For these results no separate measurements of light intensity or light absorbance, required by other methods, is needed.

We claim:
1. A portable cell for measuring the photosynthetic activity of photosynthetically active tissue, comprising:
   a housing, said housing being open at one end;
   an acoustic transducer, located within said housing;
   securing means for securing said housing, at the open end thereof, to or over a photosynthetically active specimen to be measured;
   a modulated light source;
   a continuous light source;
   first guide means for guiding modulated light from said modulated light source toward the specimen when in use; and
   second guide means for guiding continuous light from said continuous light source toward the specimen when in use.
2. A cell in accordance with claim 1, and further including means for varying the modulation frequency of said modulated light.
3. A cell in accordance with claim 1, wherein said first and second guide means comprise a bifurcated light guide having two branches terminating in a common end, said common end being adjacent to the sample when in use, wherein one of said branches carries the modulated light, and the other of said branches carries the continuous light.
4. A cell in accordance with claim 1, further including measuring means for measuring luminescent light generated by the sample, and third light guide means for guiding luminescent light from the sample to said measuring means.
5. A cell in accordance with claim 4, wherein said first, second and third guide means comprise a triple light guide having three branches terminating in a common end, said common end being adjacent to the sample when in use, wherein the first and second of said branches carry the modulated and continuous light, respectively, toward the sample, and said third branch carries the luminescent light from the sample.
6. A cell in accordance with claim 1, wherein said housing is transparent.
7. A cell in accordance with claim 3, wherein said housing is provided with an opening for said light guide.
8. A cell in accordance with claim 1, wherein said housing has an internal volume on the order of 0.05 to 2 $cm^3$.
9. A method for measuring the photosynthetic activity of photosynthetically active tissue, comprising:
   illuminating said tissue by modulated light, thereby causing said tissue to generate an acoustic wave in response thereto;
   varying the modulation frequency of said modulated light;
   converting the acoustic wave generated by the tissue being illuminated by said modulated light of varying frequency into a first photoacoustic signal by means of an acoustic transducer;
   simultaneously illuminating said tissue by modulated and by continuous light, thereby causing said tissue to generate an acoustic wave in response thereto;
   varying the modulation frequency of said modulated light;
   converting the acoustic wave generated by the tissue being illuminated by said continuous light and by said modulated light of varying frequency into a second photoacoustic signal by means of an acoustic transducer;
   comparing, by subtraction, at each modulation frequency, said first and said second signals.
10. A method in accordance with claim 9 and further including the step of comparing, by subtraction, said first and second signals as a function of time at each frequency of said modulated light.

* * * * *